United States Patent
Jow

(10) Patent No.: US 8,435,437 B2
(45) Date of Patent: May 7, 2013

(54) SETTING LASER POWER FOR LASER MACHINING STENTS FROM POLYMER TUBING

(75) Inventor: Kevin Jow, San Mateo, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 385 days.

(21) Appl. No.: 12/554,589

(22) Filed: Sep. 4, 2009

(65) Prior Publication Data

US 2011/0057356 A1   Mar. 10, 2011

(51) Int. Cl.
*B29C 35/10* (2006.01)

(52) U.S. Cl.
USPC .......................................................... 264/400

(58) Field of Classification Search .................... 264/400
See application file for complete search history.

(56) References Cited

U.S. PATENT DOCUMENTS

| | | |
|---|---|---|
| 3,476,463 A | 11/1969 | Kreuzer |
| 5,055,653 A | 10/1991 | Funami et al. |
| 5,163,952 A | 11/1992 | Froix |
| 5,380,976 A | 1/1995 | Couch, Jr. et al. |
| 5,486,546 A | 1/1996 | Mathiesen et al. |
| 5,656,186 A | 8/1997 | Mourou et al. |
| 5,670,161 A | 9/1997 | Healy et al. |
| 5,756,651 A | 5/1998 | Chen et al. |
| 5,962,007 A | 10/1999 | Cooper et al. |
| 5,968,052 A | 10/1999 | Sullivan et al. |
| 6,131,266 A | 10/2000 | Saunders |
| 6,150,630 A | 11/2000 | Perry et al. |
| 6,160,240 A | 12/2000 | Momma et al. |
| 6,260,976 B1 | 7/2001 | Endou et al. |
| 6,281,262 B1 | 8/2001 | Shikinami |
| 6,295,168 B1 | 9/2001 | Hoffnagle et al. |
| 6,433,301 B1 | 8/2002 | Dunsky et al. |
| 6,500,204 B1 | 12/2002 | Igaki |
| 6,521,865 B1 | 2/2003 | Jones et al. |
| 6,563,998 B1 | 5/2003 | Farah et al. |
| 6,585,755 B2 | 7/2003 | Jackson et al. |
| 6,696,667 B1 | 2/2004 | Flanagan |
| 6,801,368 B2 | 10/2004 | Coufal et al. |
| 6,852,946 B2 | 2/2005 | Groen et al. |
| 6,867,389 B2 | 3/2005 | Shapovalov et al. |
| 6,891,126 B2 | 5/2005 | Matile |

(Continued)

FOREIGN PATENT DOCUMENTS

| | | |
|---|---|---|
| DE | 197 45294 | 4/1999 |
| DE | 199 01530 | 7/2000 |

(Continued)

OTHER PUBLICATIONS

Krueger et al., "Getting Practical", SPIE's OE Magazine, pp. 23-25 (2004).

(Continued)

*Primary Examiner* — Yogendra Gupta
*Assistant Examiner* — Robert J Grun
(74) *Attorney, Agent, or Firm* — Squire Sanders (US) LLP

(57) ABSTRACT

Laser machining polymer tubing sections to form stents such that the power of the laser machining is adjusted for each tubing section to obtain repeatable strut widths for stents formed from different tubing sections is disclosed. A threshold power for laser machining each section is determined and the power used for machining each section is based on the threshold power.

21 Claims, 11 Drawing Sheets

U.S. PATENT DOCUMENTS

| | | |
|---|---|---|
| 6,943,964 B1 | 9/2005 | Zhang et al. |
| 6,995,336 B2 | 2/2006 | Hunt et al. |
| 7,057,135 B2 | 6/2006 | Li |
| 7,128,737 B1 | 10/2006 | Goder et al. |
| 2002/0132402 A1 | 9/2002 | Tanaka et al. |
| 2002/0160033 A1 | 10/2002 | Caplice et al. |
| 2002/0170898 A1 | 11/2002 | Ehrmann et al. |
| 2002/0190038 A1 | 12/2002 | Lawson |
| 2003/0097123 A1 | 5/2003 | Marchitto et al. |
| 2003/0153971 A1 | 8/2003 | Chandrasekaran |
| 2003/0155328 A1 | 8/2003 | Huth et al. |
| 2004/0026387 A1 | 2/2004 | Matile |
| 2004/0084607 A1 | 5/2004 | Ichihashi et al. |
| 2004/0098100 A1 | 5/2004 | Williams et al. |
| 2004/0143322 A1 | 7/2004 | Litvack et al. |
| 2004/0168298 A1 | 9/2004 | Dolan et al. |
| 2005/0087520 A1 | 4/2005 | Wang et al. |
| 2005/0111500 A1 | 5/2005 | Harter et al. |
| 2005/0157382 A1 | 7/2005 | Kafka et al. |
| 2005/0211680 A1 | 9/2005 | Li et al. |
| 2006/0033240 A1 | 2/2006 | Weber et al. |
| 2006/0120418 A1 | 6/2006 | Harter et al. |
| 2006/0224226 A1 | 10/2006 | Huang et al. |
| 2006/0287715 A1* | 12/2006 | Atladottir et al. ............ 623/1.49 |
| 2007/0034615 A1* | 2/2007 | Kleine .................... 219/121.72 |
| 2007/0142903 A1 | 6/2007 | Dave |
| 2009/0149940 A1* | 6/2009 | Wang et al. .................. 623/1.15 |

FOREIGN PATENT DOCUMENTS

| | | |
|---|---|---|
| DE | 29724852 U1 | 10/2009 |
| EP | 842 729 | 5/1998 |
| JP | 04-33791 | 2/1992 |
| JP | 07-124766 | 5/1995 |
| JP | 10-166156 | 6/1998 |
| JP | 2002-120080 | 4/2002 |
| JP | 2002-307184 | 10/2002 |
| JP | 2003-53577 | 2/2003 |
| JP | 2003-114400 | 4/2003 |
| WO | WO 99/20429 | 4/1999 |
| WO | WO 02/38325 | 5/2002 |
| WO | WO 2007/142736 | 12/2007 |

OTHER PUBLICATIONS

Lezner et al., "Photoablation with sub-10fs laser pulses", Appl. Surface Science 154-155, pp. 11-16 (2000).

Lezner et al., "Precision laser ablation of dielectrics in the 10-fs regime", Appl. Phys. A68, pp. 369-371 (1999).

International Search Report for PCT/US2010/047880, mailed Oct. 15, 2010, 7 pgs.

* cited by examiner

SETTING LASER POWER FOR LASER MACHINING STENTS FROM POLYMER TUBING

BACKGROUND OF THE INVENTION

1. Field of the Invention

This invention relates to laser machining tubing to form stents.

2. Description of the State of the Art

This invention relates to laser machining of devices such as stents. Laser machining refers to removal of material accomplished through laser and target material interactions. Generally speaking, these processes include laser drilling, laser cutting, and laser grooving, marking or scribing. Laser machining processes transport photon energy into a target material in the form of thermal energy or photochemical energy. Material is removed by melting and blow away, or by direct vaporization/ablation.

The application of ultrashort-pulse lasers for high quality laser material processing is particularly useful due to the extremely high intensity, ultrashort-pulse duration (<1 picosecond), and non-contact nature of the processing. Ultrashort pulse lasers allow precise and efficient processing, especially at the microscale. Compared with long-pulse lasers and other conventional manufacturing techniques, ultrashort pulse lasers provide precise control of material removal, can be used with an extremely wide range of materials, produce lower thermal damage, and provide the capability for very clean small features. These features make ultrashort-pulse lasers a promising tool for microfabrication, thin film formation, laser cleaning, and medical and biological applications.

However, laser machining of a substrate tends to result in unwanted heat transfer to a substrate resulting in a heat affected zone. The heat affected zone is a region on the target material that is not removed, but is affected by heat due to the laser. The properties of material in the zone can be adversely affected by heat from the laser. Therefore, it is generally desirable to reduce or eliminate heat input beyond removed material, thus reducing or eliminating the heat affected zone.

One of the many medical applications for laser machining includes fabrication of radially expandable endoprostheses, which are adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a retractable sheath or a sock. When the stent is in a desired bodily location, the sheath may be withdrawn which allows the stent to self-expand.

The stent must be able to satisfy a number of mechanical requirements. First, the stent must be capable of withstanding the structural loads, namely radial compressive forces, imposed on the stent as it supports the walls of a vessel. Therefore, the stent must possess adequate radial strength and rigidity. Radial strength, which is the ability of a stent to resist radial compressive forces, is due to strength around a circumferential direction of the stent.

Once expanded, the stent must adequately maintain its size and shape throughout its service life despite the various forces that may come to bear on it, including the cyclic loading induced by the beating heart. For example, a radially directed force may tend to cause a stent to recoil inward. Generally, it is desirable to minimize recoil. In addition, the stent must possess sufficient flexibility to allow for crimping, expansion, and cyclic loading without fracturing that would adversely affect stent performance. Finally, the stent must be biocompatible so as not to trigger any adverse vascular responses.

The structure of a stent is typically composed of scaffolding that includes a pattern or network of interconnecting structural elements often referred to in the art as struts or bar arms. The scaffolding can be formed from wires, tubes, or sheets of material rolled into a cylindrical shape. The scaffolding is designed so that the stent can be radially compressed (to allow crimping) and radially expanded (to allow deployment).

Stents have been made of many materials such as metals and polymers, including biodegradable polymeric materials. Biodegradable stents are desirable in many treatment applications in which the presence of a stent in a body may be necessary for a limited period of time until its intended function of, for example, achieving and maintaining vascular patency and/or drug delivery is accomplished.

Stents can be fabricated by forming patterns on tubes or sheets using laser machining. However, as indicated above, the use of laser machining can have adverse effects on the properties of a material, including polymers.

SUMMARY OF THE INVENTION

Various embodiments of the present invention include a method of fabricating a plurality of stents, comprising: providing a plurality of polymer tubing sections that are each formed separately by the same type of processing steps for use in forming stents of the same design; determining for each tubing section a laser power level for use in forming stents from each of the tubing sections with laser machining; and laser machining stent patterns into the tubing sections to form a plurality of stents using the laser power levels determined for each tubing section, wherein the stent patterns comprise a plurality of struts and the laser power determined for each tubing section is selected to obtain repeatable strut widths in the stent patterns formed from the different tubing sections.

Further embodiments of the present invention include a method of fabricating a plurality of stents, comprising: laser machining a plurality of polymer tubing sections to form stents comprising a plurality of struts, wherein the tubing sections are each formed separately by the same type of processing steps for use in forming stents of the same design, wherein the power of the laser machining is adjusted for each tubing section to obtain repeatable strut widths for stents formed from different tubing sections.

DETAILED DESCRIPTION OF THE INVENTION

Embodiments of the present invention relating to methods of laser machining of polymer tubing to make a stent that includes setting the power of laser system to obtain repeatable stent dimensions. Although the methods may apply to other laser machining technique, the methods are particularly relevant to ultrashort-pulse laser machining of substrates. These embodiments are suitable for fabricating fine and intricate structures of implantable medical devices such as stents. "Ultrashort-pulse lasers" refer to lasers having pulses with widths or durations shorter than about a picosecond (=$10^{-12}$). "Pulse width" refers to the duration of an optical pulse versus time. The duration can be defined in more than one way. Specifically, the pulse duration can be defined as the full width at half maximum (FWHM) of the optical power versus time.

Ultrashort-pulse lasers can include both picosecond and femtosecond (=$10^{-15}$) lasers. The ultrashort-pulse laser is clearly distinguishable from conventional continuous wave and long-pulse lasers (nanosecond ($10^{-9}$) laser) which have significantly longer pulses. In particular, embodiments of the present method employ femtosecond lasers that have pulses shorter than about $10^{-13}$ second. Representative examples of femtosecond lasers include, but are not limited to, a Ti:sapphire laser (735 nm-1035 nm) and an excimer-dye laser (220 nm-300 nm, 380 nm-760 nm).

As indicated above, embodiments of the laser machining method described above may be used in the fabrication of implantable medical devices such as stents. In general, stents can have virtually any structural pattern that is compatible with a bodily lumen in which it is implanted. Typically, a stent is composed of a pattern or network of circumferential rings and longitudinally extending interconnecting structural elements of struts or bar arms. In general, the struts are arranged in patterns, which are designed to contact the lumen walls of a vessel and to maintain vascular patency.

Figure 1:
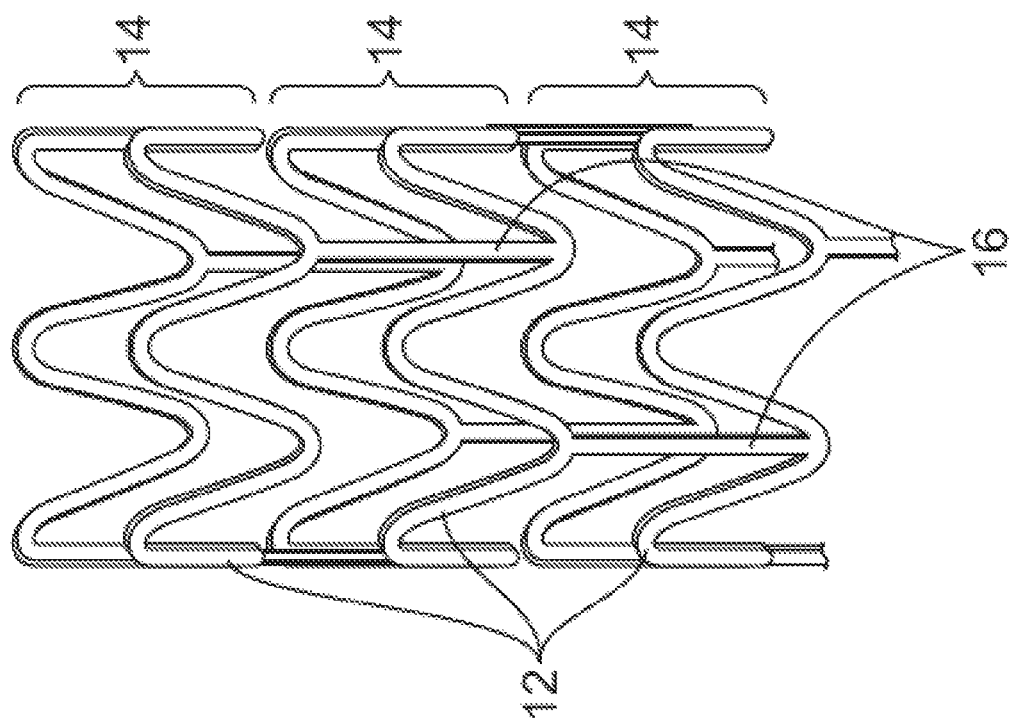
FIG. 1 depicts a stent.

An exemplary structure of a stent is shown in FIG. 1. FIG. 1 depicts a stent 10 which is made up of struts 12. Stent 10 has interconnected cylindrical rings 14 connected by linking struts or links 16. The embodiments disclosed herein are not limited to fabricating stents or to the stent pattern illustrated in FIG. 1. The embodiments are easily applicable to other stent patterns and other devices. The variations in the structure of patterns are virtually unlimited. The outer diameter of a fabricated stent (prior to crimping and deployment) may be between 0.2-5.0 mm. For coronary applications, a fabricated stent diameter is 2.5-3.5 mm. The length of the stents may be between about 6-12 mm.

The present embodiments are particular relevant to laser machining polymer substrates to form stents, however, the methods may be applicable to other materials such as metals and ceramics or composite materials composed of combinations of polymer, metal, and ceramic. Polymers can be biostable, bioabsorbable, biodegradable, or bioerodable. Biostable refers to polymers that are not biodegradable. The terms biodegradable, bioabsorbable, and bioerodable, as well as degraded, eroded, and absorbed, are used interchangeably and refer to polymers that are capable of being completely eroded or absorbed when exposed to bodily fluids such as blood and can be gradually resorbed, absorbed, and/or eliminated by the body. In addition, a medicated stent may be fabricated by coating the surface of the stent with an active agent or drug, or a polymeric carrier including an active agent or drug. The drug coating is typically applied to the stent body or scaffolding after being formed by laser machining. The coating is typically much thinner than the struts of the scaffolding, for example, the coating can be 1-5 microns in thickness while the struts can be 140-160 microns thick.

An implantable medical device, such as a stent, can be fabricated by laser machining a construct to form the device. Material is removed from selected regions of the construct which results in formation of the structure of the device. In particular, a stent may be fabricated by machining a thin-walled tubular member with a laser. Selected regions of the tubing may be removed by laser machining to obtain a stent with a desired pattern. Specifically, a beam can be translated or scanned over the surface of a tubing resulting in removal of a trench or kerf extending all the way through a wall of the tubing. When a starting and ending point of a kerf meet, the region surrounded by the kerf drops out or is removed. Alternatively or additionally, the tube can be translated and rotated to allow machining of tubing.

Figure 2:
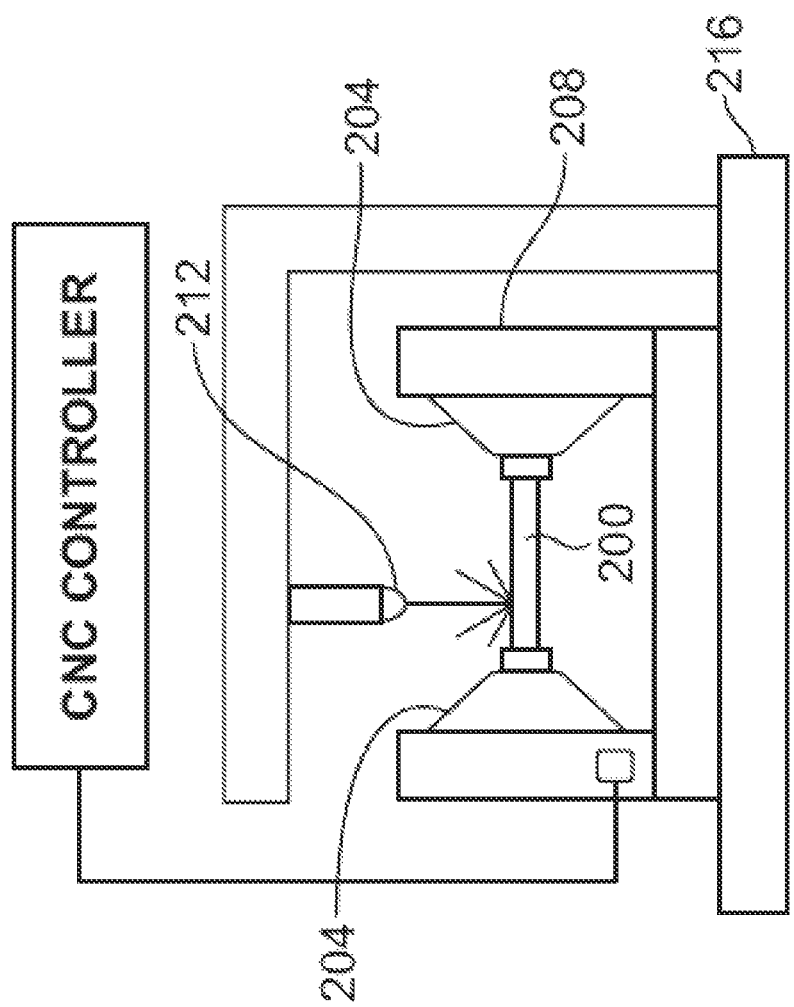
FIG. 2 depicts an embodiment of a portion of a machine-controlled system for laser machining a tube.

In exemplary embodiments, a stent can be cut from a tubing using a machine-controlled laser as illustrated schematically in FIG. 2. FIG. 2 depicts an embodiment of a portion of a machine-controlled system for laser machining a tube. In FIG. 2, a tube 200 is disposed in a rotatable collet fixture 204 of a machine-controlled apparatus 208 for positioning tubing 200 relative to a laser 212. According to machine-encoded instructions, tube 200 is rotated and moved axially relative to laser 212 which is also machine-controlled. The laser selectively removes the material from the tubing resulting in a pattern cut into the tube. The tube is therefore cut into the discrete pattern of the finished stent.

Figure 3:
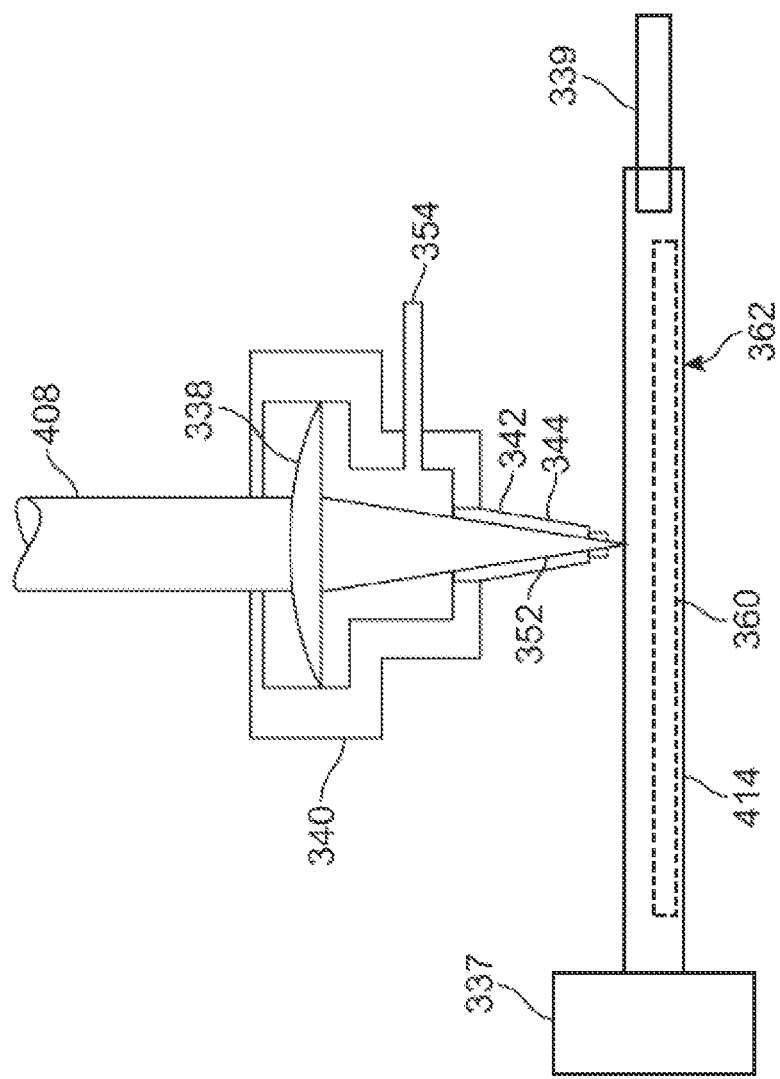
FIG. 3 depicts a close-up axial view of a region where a laser beam interacts with a tube.

FIG. 3 depicts a close-up view of a laser beam 408 interacting with a tube 414. Laser beam 408 is focused by a focusing lens 338 on tube 414. Tube 414 is supported by a controlled rotary collet 337 at one end and an optional tube support pin 339 at another end. A coaxial gas jet assembly 340 directs a cold gas jet or stream 342 that exits through a nozzle 344 that cools the machined surface as the beam cuts and ablates a substrate. The gas stream also helps to remove debris from the kerf and cool the region near the beam. Gas input is shown by an arrow 354. Coaxial gas jet nozzle 344 is centered around a focused beam 352. In some embodiments, the pressure of the supplied cooling gas is between 30 and 100 psi. An exemplary flow rate of the cooling gas is between 2 and 10 scfh. Exemplary cooling gases or process gases include helium, argon, nitrogen, or oxygen.

It may also be necessary to block focused beam 352 as it cuts through the top surface of the tube to prevent the beam, along with the molten material and debris from the cut, from impinging on the inside opposite surface of tube 414. To this end, a mandrel 360 supported by a mandrel beam block 362 is placed inside the tube and is allowed to roll on the bottom of the tube 414 as the pattern is cut. This acts as a beam/debris block protecting the far wall inner diameter.

The present invention is applicable to femtosecond pulsed lasers having pulse widths of 5-10 fs, 10-80, 80-120 fs, 120-500, or 500-1000 fs. It is also believed the invention is applicable to lasers with pulse widths greater than 1000 fs (1 ps), greater than 10 ps, in particular, 10-15 ps.

The repetition rate used for laser machining polymers for stents with a femtosecond laser is generally between 1 and 5 kHz. The energy per pulse of such laser machining is generally 2-1000 µJ, more narrowly, 20-30 µJ. The fluence of such laser machining is generally 1-20 J/cm$^2$, or more narrowly, 5-15 J/cm$^2$. The average power per pulse or power of a beam can be 10-1000 mW, or more narrowly 50-150 mW. Fixed and variable wavelength lasers may be used for laser machining polymers. Exemplary fixed wavelength lasers may have wavelengths at 248 nm, 532 nm, or 800 nm.

The embodiments of the present invention relate to determining the power of the femtosecond laser used for laser machining a polymer tubing. A power is determined for a tubing section that reduces or eliminates undesirable cutting affects. The power determination also provides repeatable stent dimensions, such as strut widths, as compared to other tubing sections processed separately prior to laser machining.

Embodiments of the method include providing a plurality of polymer tubing sections that are each formed separately by the same type of processing steps for use in forming stents of the same design. The same design refers to features such as the stent pattern and the dimensions of the structural elements or struts of the stent pattern including thickness and width. Other features of a design include mechanical properties such as radial strength and fracture toughness. Additional features include morphology properties such as polymer orientation, crystallinity, and the size of crystallites of a semicrystalline polymer. The processing of stent precursor constructs or tubing sections is performed so that such features are as close as possible for tubing sections made at different times.

For each tubing section, a laser power level is determined for use in forming stents from each of the tubing sections with laser machining. The method further includes laser machining stent patterns into the tubing sections to form a plurality of stents using the laser power levels determined for each tubing section. The stent patterns include a plurality of struts. The laser power determined for each tubing section is selected to obtain repeatable strut widths in the stent patterns formed from the different tubing sections.

The inventors had used a femtosecond laser (120 fs, fluence=10±5) to machine PLLA tubes to form stents. The machining power was set to a value that was believed to be significantly higher than a minimum value required to machine through the tubing to form struts. The inventors used the same power for all lots of tubing. A "lot" of tubing refers to a section of tubing made or processed at a given time, for example, a lot of tubing extruded and then radially expanded.

Specifically, the inventors unexpectedly found that laser machining different lots with the same power with the same laser yielded stents with different quality and strut widths. The different lots were of the same material, PLLA, and all had the same wall thickness. The different lots were made at different times either with the same processing conditions or only slightly different processing conditions.

The inventors observed that the quality of a machined stent and stent dimensions obtained from laser machining different lots of tubing was extremely sensitive the laser power. "Quality" refers to several aspects of a cut stent pattern. One aspect is the degree of smoothness of the cut. A poor quality cut can have rough portions on a cut surface, such as flashes which refers to un-cut material that is torn from the excess cut away sections. Another aspect of a poor quality cut is "glitter" which refers to re-deposited material as particles large enough to create a reflective surface. Excess melting in portions of the stent pattern are another characteristic of a poor quality cut. Another characteristic of a poor quality stent pattern are islands, which are portions of tubing that are not intended to be part of the stent pattern that do not fall out of the cut pattern since a region surrounded by a kerf is still attached to a strut. Islands may result when the power is insufficient for a beam to consistently cut all the way through a tubing wall as it travels around a region to be removed.

The differences in machining the different lots of tubing are a sensitivity to power likely arising from variations in morphology of the polymer in the different lots of tubing. The difference in morphology can arise from even the slightest differences in processing conditions. Even slight differences in process conditions will likely result in such morphology variations between lots of tubing. However, it was unknown to the inventors that such minor variations in processing conditions prior to machining could have such a dramatic affect on cutting quality and strut dimensions. Inventors have found it essential to compensate for unexpected sensitivity to these variations through adjustment of the power for different lots of tubing.

The processing referred to above includes forming a tube from a polymer resin using an extrusion process followed by radially expanding and axial elongating the tube. A stent is formed by laser machining a stent pattern in the expanded and elongated tube. The tube is radially expanded and axially elongated to increase the radial strength and fracture toughness of the tube and a stent made therefrom.

A semicrystalline polymer, such as PLLA, includes crystalline regions separated or surrounded by amorphous regions. Morphology includes, but is not limited to, degree of crystallinity, molecular orientation of polymer chains, and crystallite size. Molecular orientation refers to the relative orientation of polymer chains along a longitudinal or covalent axis of the polymer chains. The orientation can refer to the orientation of crystalline lamella and to the orientation of polymer chains in the amorphous regions.

With regard to making a tube by extrusion, representative examples of extruders include single screw extruders, intermeshing co-rotating and counter-rotating twin-screw extruders and other multiple screw masticating extruders. For example, tubing for a stent can be formed with a 1" single screw extruder. A temperature range in the extruder is at least 20° C. above the Tm of the polymer. For example, an exemplary temperature range for PLLA extrusion is 200-225° C. Other exemplary processing conditions for PLLA tubing include a residence time in the extruder of approximately 10 min, quench in room temperature water bath, a die/quench distance of ¾ in, a pull rate of 16 ft/min, a barrel pressure of 2000 psi, and a draw down ratio approximately 3:1 (ID die to ID of drawn tube).

A polymeric tube is radially expanded and axially elongated by increasing the pressure inside the tube and applying a tensile force along the cylindrical axis of the tube, respectively. The pressure inside of the tube is increased by conveying a fluid into the tube to increase the internal pressure in the tube. Preferably, the tensile force is applied at one end while holding the other end stationary. The tube is heated to a temperature between the glass transition temperature (Tg) and the melting temperature (Tm) of the polymer to allow the radial expansion and axial elongation of the tube.

At the start of the process, the tube is positioned in a cylindrical member or mold. The process parameters are adjusted so that the tube expands against the inside surface of the mold so that the outer diameter of the expanded tube is the inside diameter of the mold. One end of the tube is sealed or blocked and a gas such as air, nitrogen, oxygen, argon, etc. is conveyed in the other end of the polymer tube to increase the pressure in the tube.

The tube is heated by a heating source such as a nozzle or nozzles blowing a warm gas onto a portion of the tube. The nozzle(s) are translated along the cylindrical axis of a the tube from a proximal end to a distal end, blowing warm gas onto an axial section or portion of the mold as it translates which heats the axial section or portion of the mold and the axial section or portion of the tube within the mold. The temperature and nozzle rate are adjusted so that as the nozzle translates, the heated portion expands. The radial expansion follows the translating nozzle and propagates along the cylindrical axis of the tube. As the nozzle translates, the an end of the tube is pulled at a specified rate, which is preferably constant.

The nozzle rate and pull rate are adjusted so that expansion and axial elongation start at the same time and are completed at the same time. Additionally, the nozzle rate and pull rate are preferably constant since the properties of a deformed polymer generally depend on the rate of deformation.

Prior to the expansion and elongation, the tube is preheated close to the deformation temperature. Pre-heating can be performed by a nozzle translated along the length of the tube without the increased pressure and the tension. After the expansion and elongation is completed, the polymer tube is cooled or allowed to cool to below its Tg either before or after decreasing the pressure and/or decreasing tension. Cooling the tube helps insure that the tube maintains the proper shape, size, and length following its formation. A section of tubing expanded in the way described is considered a "lot" of tubing.

Any slight variations in the processing conditions from lot to lot can result in differences in morphology from lot to lot. Variations can result from adjustments to processing conditions so that the expansion occurs in the manner desired, as described above. Such slight variations in processing conditions unexpectedly alter the power requirements for obtaining a quality machined stent with repeatable strut dimensions.

Exemplary processing conditions for a PLLA tube deformation include a deformation temperature of 75-130° C., an expansion pressure of 110-140 psi, a nozzle translation rate 0.2-1.2 mm/s, a pull rate of 0.4-4.0 mm/s.

The percent degree of radial expansion (% RE) of a tube is 100%×(Inside Diameter of Expanded Tube/Original Inside Diameter of Tube−1). The percent degree of axial elongation (% AE) is: 100%×(Length of Elongated Tube/Original Length of Tube−1). Exemplary % RE are 200-500% and % AE are 20-200%. The degree of crystallinity of exemplary expanded PLLA tubes and stents made therefrom are 20-50%, or more narrowly, 45-50%.

In addition to selecting the power for quality and repeatability, power is also selected to reduce the heat affected zone of a machined substrate. As mentioned above, the heat affected zone is a region on the target material that is not removed, but is affected by thermal energy from the laser. In the heat affected zone, the properties of material in the zone vary as a function of distance. Stent performance may be increased by reducing or eliminating the variation in properties of the heat affected zone. Stent performance includes having a high radial strength sufficient maintain patency, low recoil, and resistance to cracking upon crimping and deployment.

The inventors have found that the variation of properties in the heat affected zone depends on the power. As the power increases the depth and variation in properties changes. This has been demonstrated by nanoindentation results. Therefore, a lower power is preferable.

In some embodiments of the invention, a selected machining power for making a stent from a selected tubing lot includes determining an a approximate threshold power level for the laser to cut a kerf or channel all the way through the tubing wall. The threshold power can correspond to the power level that allows the laser beam to cut through a length of tubing completely when the beam in scanned over the length, in spite of slight variations in the thickness and properties in different portions of the tubing. A power level that results in portions along the length that are cut all the way through and portions along the length which are not when the laser is scanned along the length is below the threshold power. The length of such a section for determining the threshold power may be 0.2-20 mm, or more narrowly, 0.2-0.5 mm, 0.5-1 mm, 1-5 mm, 5-10 mm, or 10-20 mm.

Each lot of tubing can have a different threshold power level. Any difference or change to the material such as thickness, percent radial expansion, percent axial elongation, or crystallinity may alter the threshold power. The inventors have found that different lots of PLLA tubing have different threshold power levels.

In some embodiments, the threshold power may be the stent cutting power which is the power used to laser machine stents from the lot of tubing. In other embodiments, the stent cutting power level may be above the threshold power. In such embodiments, exemplary stent cutting power level can be A ×threshold power, where "A" is between 100% and 120%, or more narrowly, 100% and 110%. "A" can be between 100% and 102%, 102% and 105%, 105% and 108%, 108% and 112%, or 112% and 120%. In other embodiment, A can be between 120-150%, or greater than 150%.

The inventors have found that a preferable stent cutting power level is 110% of the threshold power level. In some embodiments, a stent pattern cut using the power is free or almost free of flash, glitter, or melted portions.

In some embodiments, the threshold power can be determined by first selecting an initial power level that is believed to cut a kerf or channel all the way through the tubing wall, as described above. The presumption is then verified by machining a length of the tubing at the initial power level. Then, a length of tubing is machined at a power level lower than the initial power and the machining portion is inspected. The process is repeated by making discrete steps downward in power until a power level ("sub-threshold power") is found that results in portions along the machined length that are cut all the way through and portions are not after the laser is scanned over length.

In some embodiments, the lowest power level selected that is greater than the sub-threshold power can be selected as the threshold power. In other embodiments, one or more additional power levels between the two lowest power levels can be tested to obtain a more accurate value of the threshold power.

EXAMPLES

The examples and experimental data set forth below are for illustrative purposes only and are in no way meant to limit the invention. The following examples are given to aid in understanding the invention, but it is to be understood that the invention is not limited to the particular materials or procedures of examples.

Example Set 1

The following set of examples describes results of determining laser machining power for four lots of PLLA tubing. Each lot of tubing was formed from an extrusion process from 100% PLLA resin. The dimensions of the tubing, the extruded dimensions, are: outside diameter (OD)=0.066 inch and inside diameter (ID)=0.025 inch. The extruded PLLA tubes were radially expanded according the process described above. The target % RE was 400%.

Titanium-Sapphire fixed wavelength lasers were used with a wavelength of 800 nm. The pulse widths of the lasers ranged from 95-120 fs with a repetition rate of 5 kHz. The fluence was between $10\pm5$ kJ/cm$^2$. For a given laser, it was found that each lot had a different selected machining power was determined. Additionally, for a given lot of tubing, the selected machining power was different for each laser. The selected machining powers (110% ×threshold power) determined for various lots of tubing were between 90-140 mW.

Table 1 provides the selected machining powers that were determined for the four lots of tubing for three different lasers. The deformation parameters for each lot of tubing is given in Table 2.

TABLE 1

Selected machining power for tubing determined for four lots and three lasers.

|  | Lot 1 Power (mW) | Lot 2 Power (mW) | Lot 3 Power (mW) | Lot 4 Power (mW) |
|---|---|---|---|---|
| Laser 1 | 140 | 135 | 128 | 140 |
| Laser 2 | 105 | 110 | 90 | — |
| Laser 3 | — | 130 | 128 | 100 |

TABLE 2

Deformation parameters for lots of tubing listed in Table 1.

| Deformation Parameters | Lot 1 | Lot 2 | Lot 3 | Lot 4 |
|---|---|---|---|---|
| Expand Heat (F.) | 166 | 185 | 178 | 180 |
| Expand Air Flow (scfh) | 60 | 60 | 60 | 60 |
| Pre-heat Dwell (sec) | 32 | 30 | 38 | 32 |
| Heat Nozzle Speed (mm/s) | 0.32 | 0.30 | .38 | .32 |
| Expand Pressure (psi) | 110 | 130 | 110 | 115 |
| Number of Passes | 1 | 1 | 1 | 1 |
| Initial Tension Position (mm) | 25 | 25 | 25 | 25 |
| Pre-Tension (Grams) | 180 | 180 | 180 | 180 |
| Set Heat (F.) | 32 | 32 | 32 | 32 |
| Set Air Flow (scfh) | 20 | 20 | 20 | 20 |
| Set Heat Dwell (min) | 0 | 0 | 0 | 0 |
| Cool Time (sec) | 30 | 30 | 30 | 30 |
| Tubing Start OD (thou in) | 66 | 66 | 66 | 66 |
| Tubing Start ID (thou in) | 25 | 25 | 25 | 25 |
| Tubing End OD (thou in) | 136 | 136 | 136 | 136 |
| Tubing End ID (thou in) | 124.2 | 124.2 | 124.2 | 124.2 |

Example Set 2

The affect of power and the degree of radial expansion on strut width was studied. The inventors observed that a repeatable strut width was not obtained when the same power was used to machine different lots of tubing. The inventors also observed that for a given power, different strut widths were obtained from tubing with different degrees of radial expansion. The laser power had to be adjusted each time to obtain a desired strut width.

The affect of power and the degree of radial expansion was studied by laser machining two PLLA tubes with two different % RE, 300% and 400%, at several power levels. The strut widths of each of the stents were measured to determine the affect of power on strut width. The expanded inside and outside diameter of the expanded tubes are approximately the same.

Figure 4:
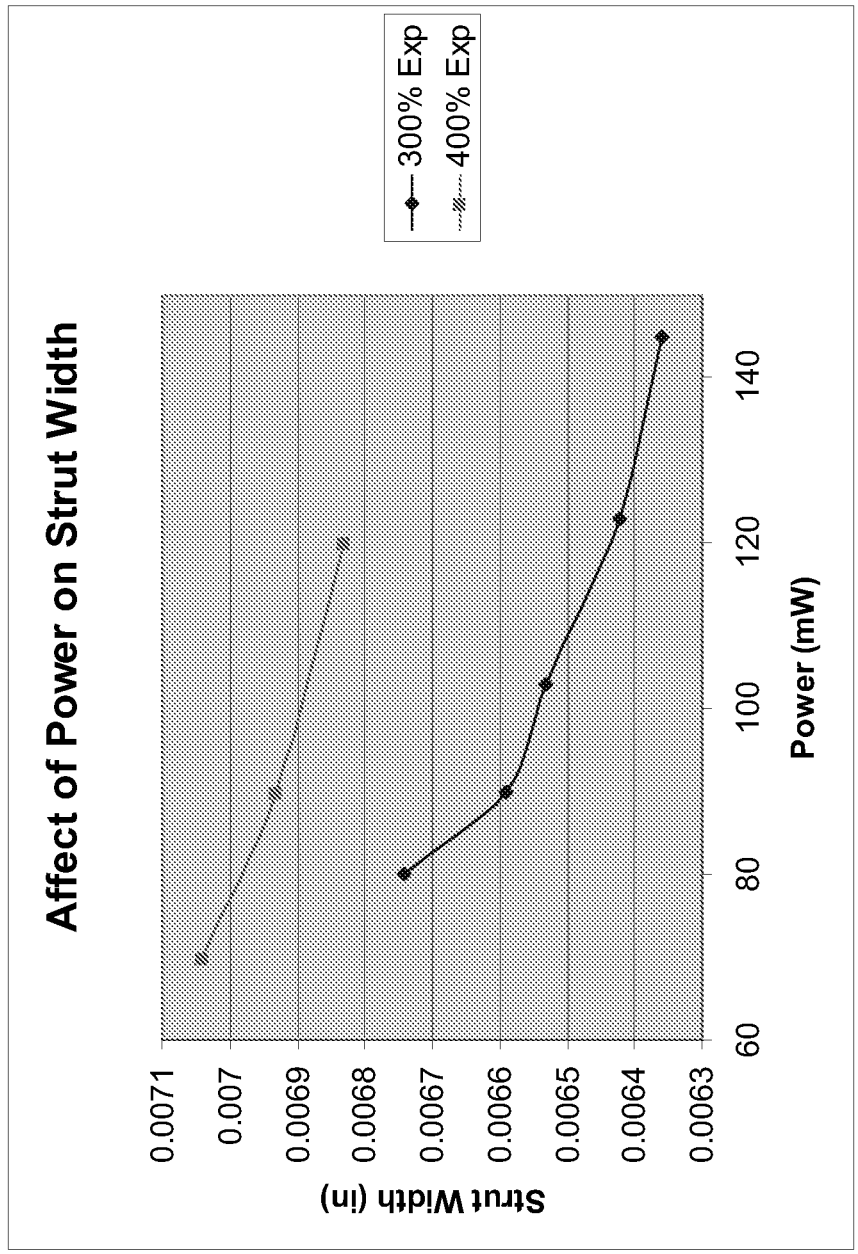
FIG. 4 is a plot of the strut width versus laser power for tubing made with two different degrees of radial expansion.

A summary of the strut width data is shown in Table 3 and the data is plotted in FIG. 4.

TABLE 3

Laser machining data showing dependence of strut width on power and radial expansion.

| % RE | Power | Strut width (inch) |
|---|---|---|
| 300 | 80 | 0.00674 |
| 300 | 90 | 0.00659 |
| 300 | 103 | 0.00653 |
| 300 | 123 | 0.00642 |
| 300 | 145 | 0.00636 |
| 400 | 70 | 0.00704 |
| 400 | 90 | 0.00693 |
| 400 | 120 | 0.00683 |

The data in Table 3 and FIG. 4 demonstrate that:
1. As the power increases when laser machining a given lot of tubing, the strut width decreases. The trend was apparent on tubing with two different radial expansions studied.
2. The degree of radial expansion affected strut width.

The two groups were cut with the same laser and the same stent pattern program. The measurements were taken with a Keyence optical microscope at 200×, calibrated to a pin gauge. Power dependence shows that if same power is used for all tubes, different strut widths will be obtained.

Example Set 3

Stent patterns cut from a PLLA tube at two different power levels showed the effect of power on the quality of cutting. The degree of radial expansion of the PLLA tubes was 400%. The expanded tubing had a 0.136 in OD and a 0.006 inch nominal wall thickness. The pulse width of the laser was 92 fs and the height of cooling nozzle blowing helium gas was 0.35. Exhaust was 1150 ft/min. Stent patterns were cut at two power levels, 70 mW and 90 mW.

Figure 5A:
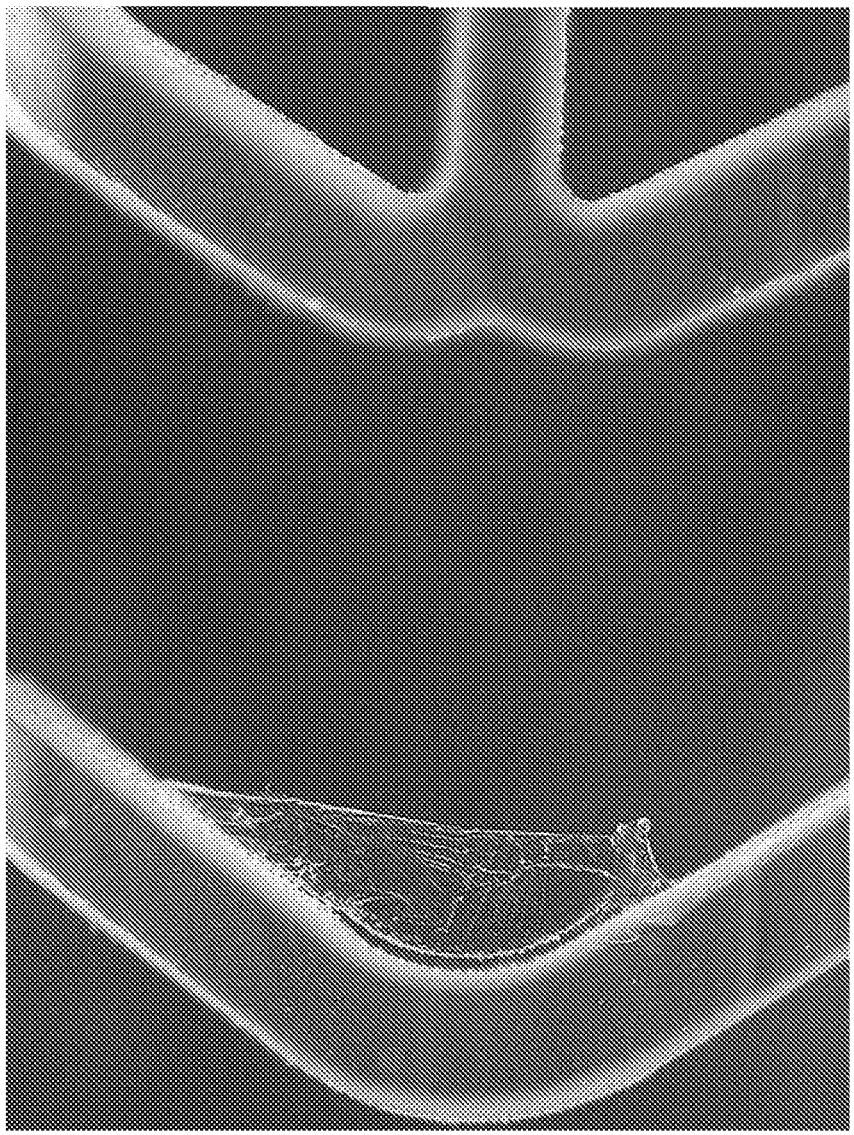
FIGS. 5A-D depict images of a stent pattern formed using a laser using 70 mW of power.
Figure 5B:
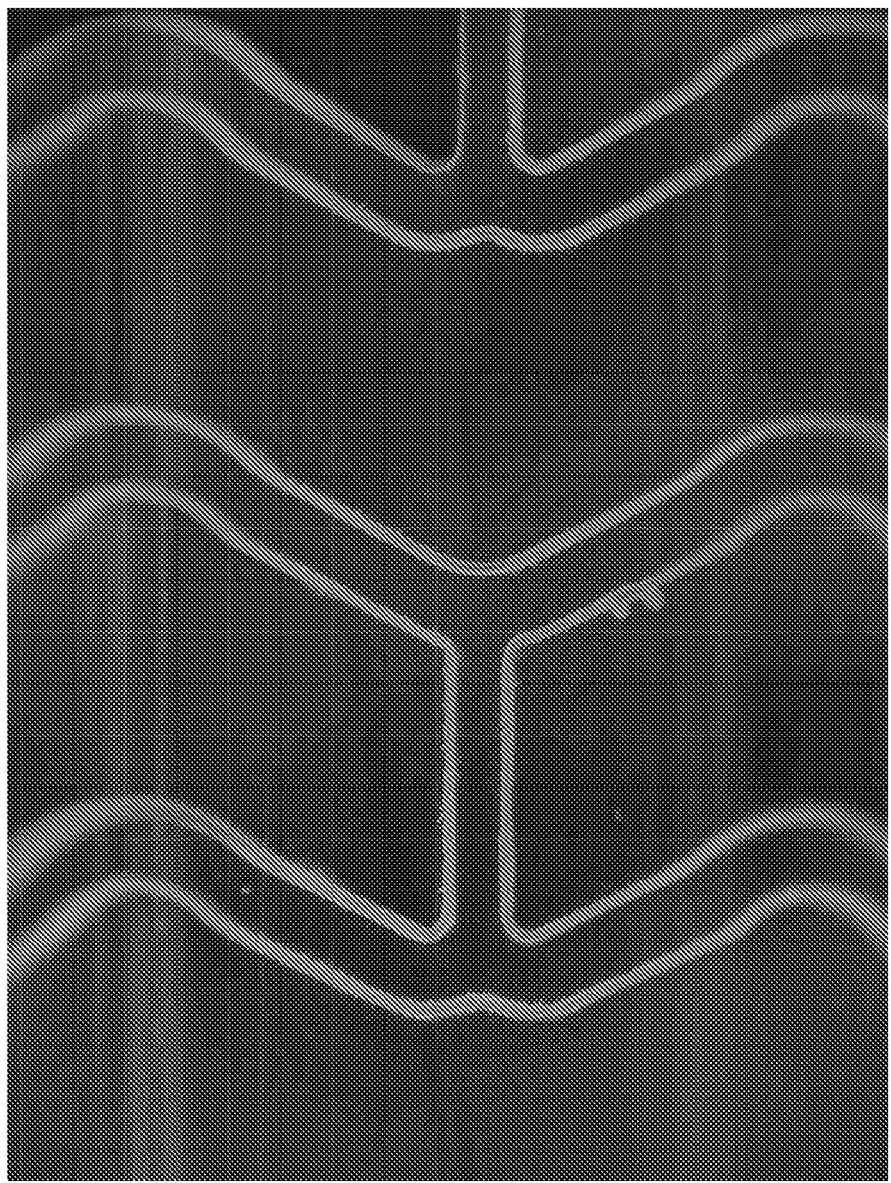
Figure 5C:
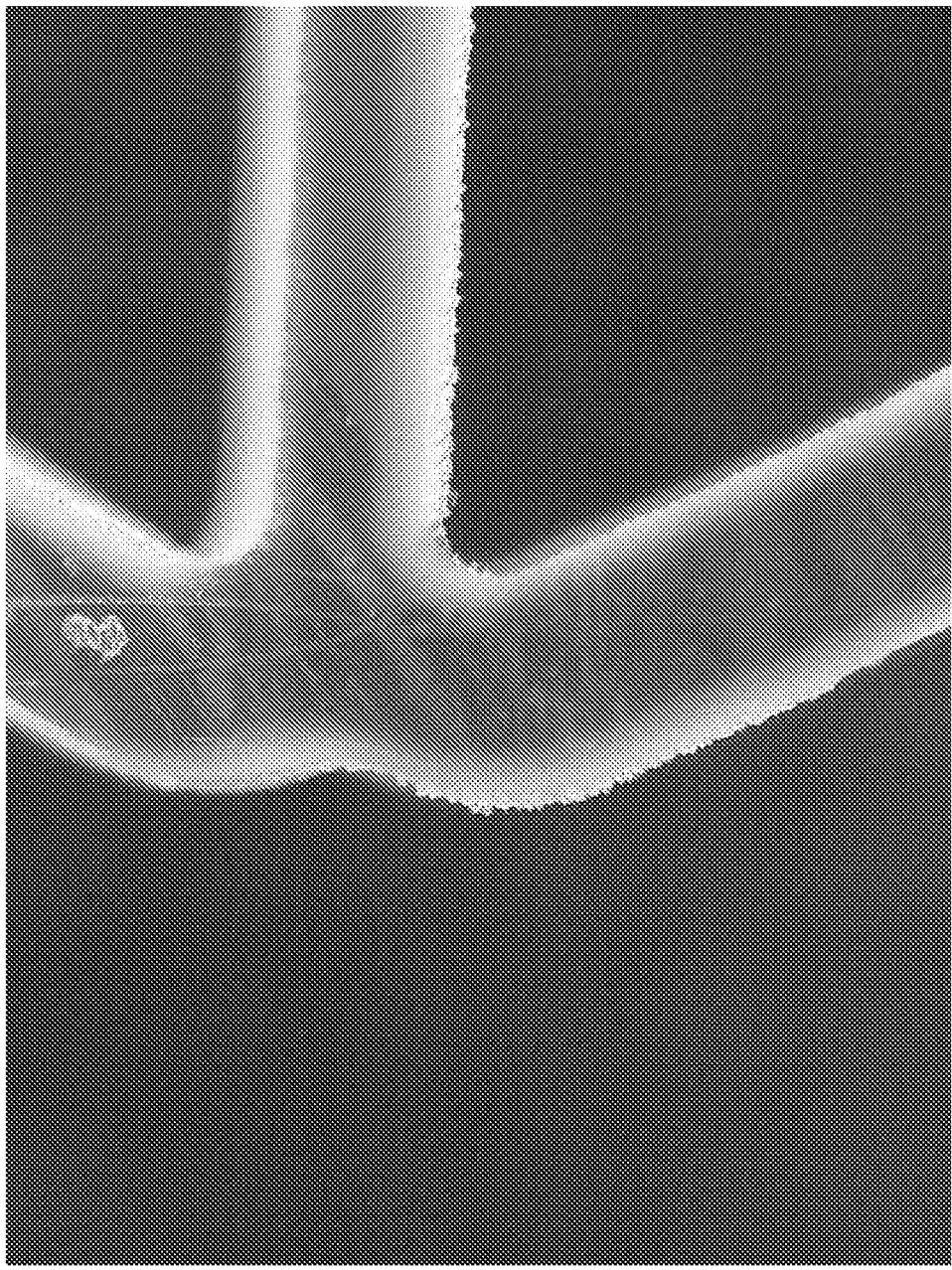
Figure 5D:
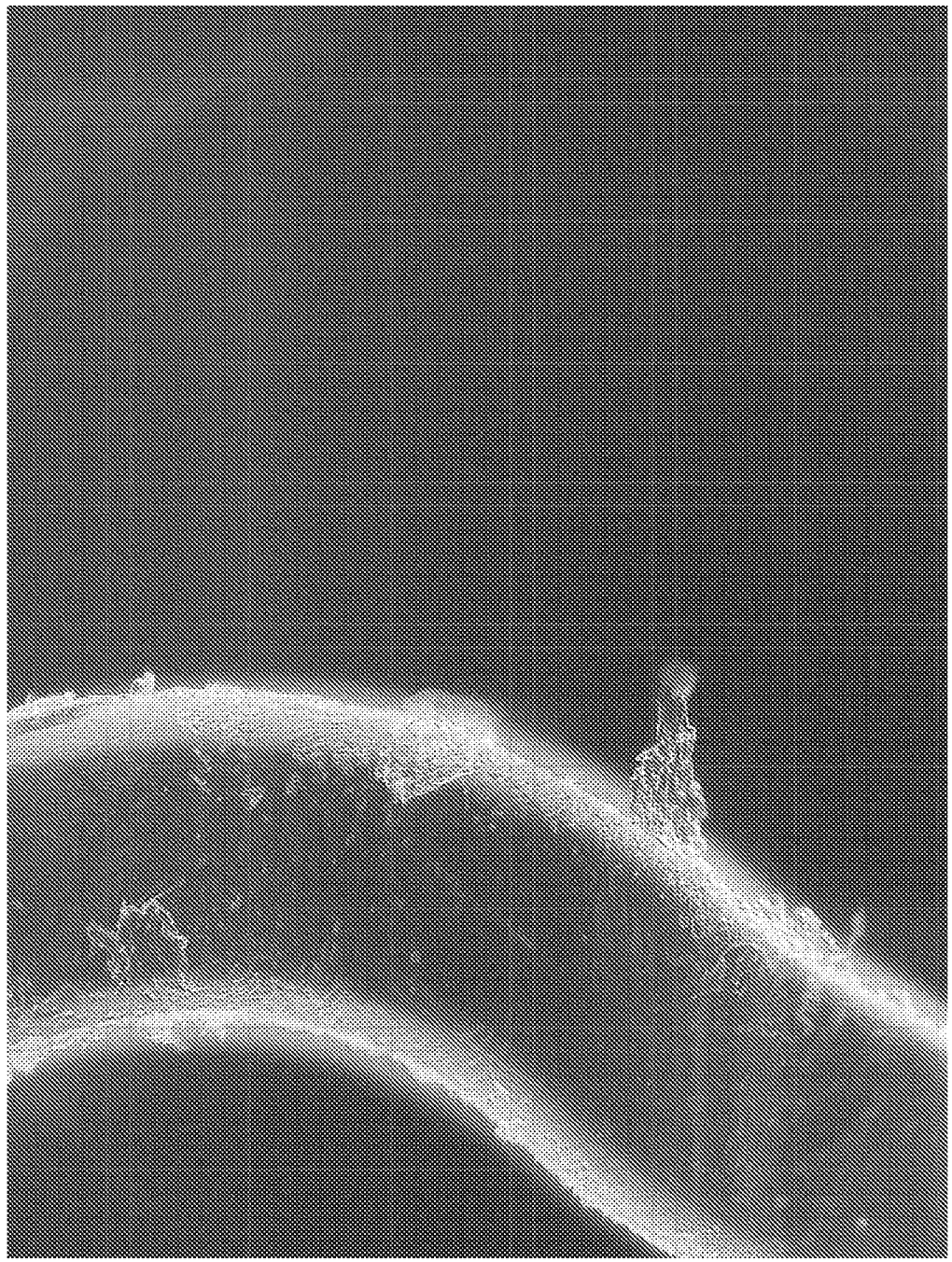

The stent patterns cut with a power level of 70 mW and an helium cooling flow gas of 4 scfh had flashes, roughness, and islands. FIGS. 5A-D are exemplary images of portions of the stent patterns cut under these conditions. FIG. 5A illustrates an island and flash. FIG. 5B shows flash. FIG. 5C shows roughness. FIG. 5D shows flash and glitter.

Figure 6A:
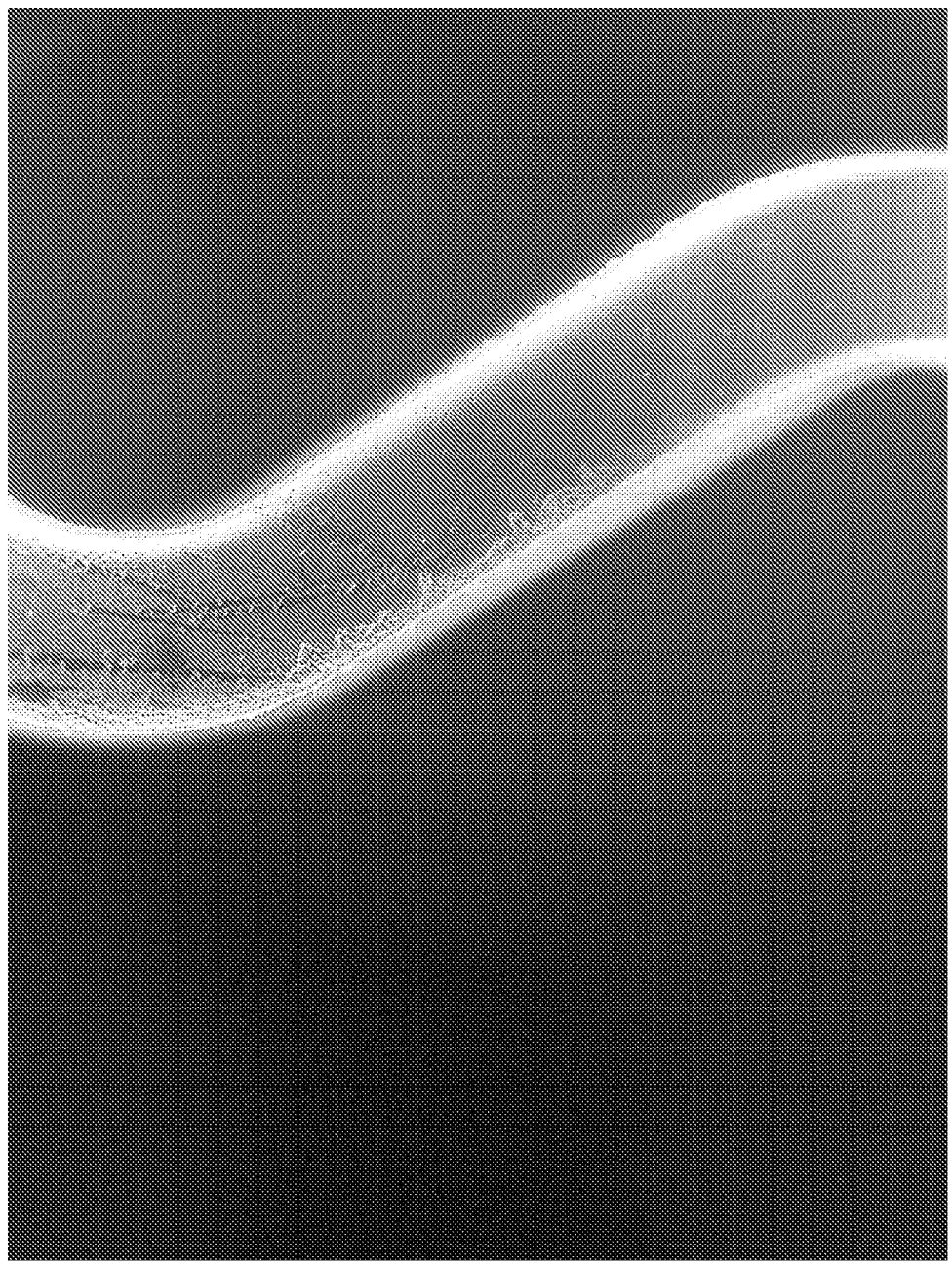
FIGS. 6A-C depict images of a stent pattern formed using a laser using 90 mW of power.
Figure 6B:
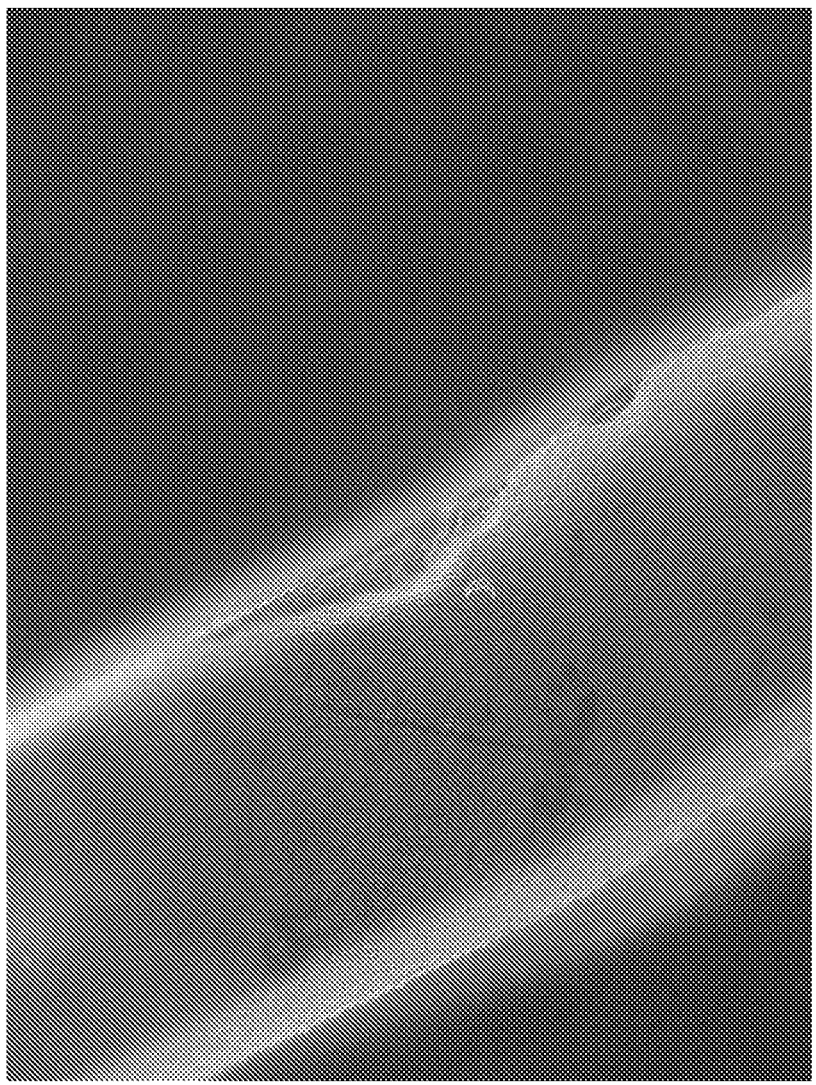
Figure 6C:
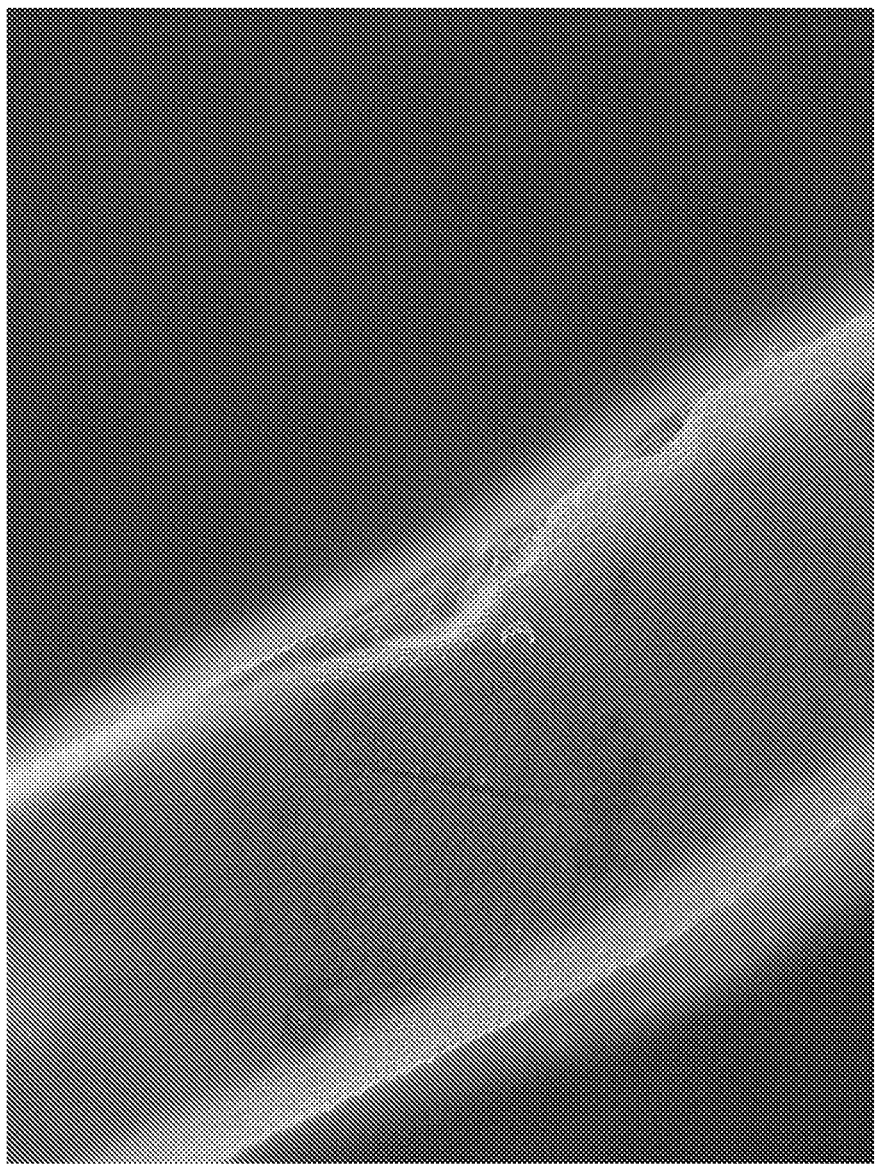

FIGS. 6A-C are exemplary images of portions of the stent patterns cut with a power level of 90 mW. FIGS. 6A-B are portions cut with helium cooling gas flow of 4 scfh and FIG. 6C are portions cut with the flow at 6 scfh. As shown in FIGS. 6A-B, the flash were no longer present, however, melt and glitter were. The helium flow was raised from 4 to 5, but the melt and glitter remained (not shown). As shown in FIG. 6C, after the flow was increased to 6 scfh, the melt and glitter were no longer present.

As used herein, "substantially the same" or "almost the same" can refer to within 0.01% to 5%.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of fabricating a plurality of stents, comprising:
providing a plurality of polymer tubing sections that are each formed separately by the same type of processing steps for use in forming stents of the same design,
wherein each of the tubing sections are made of the same polymer and have the same wall thickness,
wherein the quality and dimensions of stents obtained from the laser machining of the different tubing sections are sensitive to the laser power such that laser machining the different tubing sections with the same power yields stents with different quality and strut widths,
wherein the sensitivity is due to variations in morphology between the different tubing sections arising from slight differences in conditions of the processing steps;
determining for each tubing section from a length of each tubing section an average laser power level for use in forming stents from each of the tubing sections with laser machining; and
laser machining stent patterns into the tubing sections to form a plurality of stents using the laser power levels determined for each tubing section,
wherein the stent patterns comprise a plurality of struts and the average laser power determined for each tubing section is selected to compensate for the sensitivity to the variations through adjustment of the power for the different tubing sections to obtain repeatable strut widths which are the same in each of the stent patterns formed from the different tubing sections.

2. The method of claim 1, wherein the laser power level for each tubing section is A×a threshold power, the threshold power being a minimum power that provides a channel completely through the wall of a selected tubing section and A is between 100 and 120% and is the same for each tubing section.

3. The method of claim 2, wherein A is between 108% and 112%.

4. The method of claim 1, wherein the laser power level is different for at least two of the tubing sections.

5. The method of claim 1, wherein each tubing section is made of the same material and has the same wall thickness and outer diameter.

6. The method of claim 1, wherein a pulse width, repetition rate, and fluence are the same in the laser machining of each of the tubing sections.

7. The method of claim 1, wherein the processing steps comprise tubing extrusion and radial expansion of the extruded tubes, the method further comprising extruding a plurality of tubing sections and radially expanding the extruded tubing sections to form the plurality of tubing sections.

8. The method of claim 1, wherein the laser is a femtosecond laser with a pulse width between 95-120 fs.

9. The method of claim 1, wherein the tubing sections are made of PLLA.

10. The method of claim 1, wherein the stents formed using the determined laser power levels are free of defects including flash, glitter, and melted portions.

11. The method of claim 1, wherein the laser machining parameters include a pulse width of 95-120 fs, a repetition rate is 2.5-5 kHz, a power level of 0.2-0.3 mW, and a fluence of 5-15 J/cm$^2$.

12. A method of fabricating a plurality of stents, comprising:
laser machining a plurality of polymer tubing sections to form stents comprising a plurality of struts,
wherein the tubing sections are each formed separately by the same type of processing steps for use in forming stents of the same design,
wherein each of the tubing sections are made of the same polymer and have the same wall thickness,
wherein the quality and dimensions of stents from the different tubing sections are sensitive to the laser power such that laser machining the different tubing sections with the same power yields stents with different quality and strut widths,
wherein the sensitivity is due to variations in morphology between the different tubing sections arising from slight differences in conditions of the processing steps,
wherein an average power of the laser machining is adjusted for each tubing section to compensate for the sensitivity to the variations through selection of the power from a length of each of the different tubing sections that results in obtaining repeatable strut widths which are the same for each of the stents formed from different tubing sections.

13. The method of claim 12, wherein each tubing section is made of the same semicrystalline polymer material and each tubing section has the same wall thickness and outer diameter.

14. The method of claim 12, wherein the adjusted power for each tubing section is different from the adjusted power for other tubing sections.

15. The method of claim 12, wherein at least one processing parameter of the processing steps of each tubing section differ and the morphology of the processed tubing sections depends on the at least one parameter.

16. The method of claim 12, wherein the processing steps comprise tubing extrusion and radial expansion of the extruded tubes, the method further comprising extruding a plurality of tubing sections and radially expanding the extruded tubing sections to form the plurality of tubing sections.

17. The method of claim 12, wherein laser machining is performed with a laser having a pulse width of 80-120 fs.

18. The method of claim 12, wherein laser machining is performed with a laser having a pulse width of 10-15 ps.

19. A method of fabricating a plurality of stents, comprising:
providing a plurality of polymer tubing sections that are each formed separately by the same type of processing steps,
wherein the tubing sections are for use in forming stents of the same design of stent patterns comprising a plurality of struts,
wherein the stents have a desired strut width for the struts of stents to be formed from the tubing sections;
wherein each of the tubing sections are made of the same polymer and have the same wall thickness,
wherein the quality and dimensions of stents obtained from the laser machining of the different tubing sections are sensitive to the laser power such that laser machining the different tubing sections with the same power yields stents with different quality and strut widths, wherein the sensitivity is due to variations in morphology between the different tubing sections arising from slight differences in conditions of the processing steps, wherein for each tubing section the method further comprises:
- determining from a length of the tubing section an average laser power that provides the desired strut width when used to form stents from the tubing section with laser machining; and
- using laser machining to form a plurality of stents from the tubing section having the desired strut width with the average laser power determined for the tubing section, wherein the determining of the average laser power for each tubing section compensates for the sensitivity to the variations which results in stents formed from the different tubing sections having the desired strut width.

20. The method of claim 19, wherein determining from a length of each tubing section an average laser power that provides the desired strut width when used to form stents from the tubing section with laser machining comprises:
- determining a threshold power for a laser used for the laser machining to cut all the way through the wall of the length of the tubing section, and
- selecting the average laser power level to be equal to or greater than the determined threshold power level.

21. The method of claim 20, wherein the average laser power is between 100% and 120% of the threshold power.

* * * * *

UNITED STATES PATENT AND TRADEMARK OFFICE
CERTIFICATE OF CORRECTION

| | | |
|---|---|---|
| PATENT NO. | : 8,435,437 B2 | Page 1 of 1 |
| APPLICATION NO. | : 12/554589 | |
| DATED | : May 7, 2013 | |
| INVENTOR(S) | : Jow | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 504 days.

Signed and Sealed this
Sixth Day of January, 2015

Michelle K. Lee
*Deputy Director of the United States Patent and Trademark Office*